United States Patent [19]

Grimard et al.

[11] Patent Number: 5,713,857
[45] Date of Patent: Feb. 3, 1998

[54] SEQUENTIAL STOPPER

[75] Inventors: Jean Pierre Grimard, Vif; Hubert Jansen, Haute Jarrie, both of France

[73] Assignee: Becton Dickinson France, S.A., Le Pont de Claix, France

[21] Appl. No.: 672,857

[22] Filed: Jun. 28, 1996

[51] Int. Cl.$^6$ .................................................. A61M 37/00
[52] U.S. Cl. ........................... 604/82; 604/89; 604/218
[58] Field of Search .............................. 604/82, 89, 90, 604/191, 218, 236, 238

[56] References Cited

U.S. PATENT DOCUMENTS

| | | | |
|---|---|---|---|
| 4,929,230 | 5/1990 | Pfleger | 604/90 |
| 5,374,249 | 12/1994 | Haber et al. | 604/91 |
| 5,489,266 | 2/1996 | Grimard | 604/89 |

*Primary Examiner*—John D. Yasko
*Attorney, Agent, or Firm*—V. A. Castiglione

[57] ABSTRACT

A sequential stopper having structural features for facilitating substantially complete delivery of fluid held within a syringe barrel. The sequential stopper features a stopper body having a cylindrical side wall, proximal and distal ends, and one or more circumferentially-disposed sealing elements thereabout. One of the circumferentially-disposed sealing elements may be located adjacent the proximal end of the stopper body. An elongate hollow chamber is disposed within the stopper body parallel to the longitudinal axis of the stopper body. A pair of longitudinal sealing elements are disposed on the cylindrical side wall of the stopper body and are separated on the sidewall by a distance greater than a maximum width displayed by the elongate hollow chamber disposed within the stopper body. A recessed surface is disposed between the longitudinal sealing elements adjacent the proximal end of the stopper body. In one embodiment, the recessed surface is formed as a sloping surface extending obliquely from the proximal end of the stopper body towards the cylindrical side wall of the stopper body. A distally-directed conically-shaped projection is located at the distal end of the stopper body. The projection includes a wedge formed through a portion of the conically-shaped projection. Fluid force exerted on the proximal end of the stopper body will be directed towards the sloping surface. Continued fluid force will cause collapse of the cylindrical side wall in the area located between the longitudinal sealing elements, thereby establishing a fluid conduit between the proximal and distal ends of the stopper body. The distally-directed conically-shaped projection prevents accumulation of fluid between the distal end of the stopper body and the internal shoulder located at the distal end of the syringe barrel, while the wedge permits fluid passing through the fluid conduit to exit the syringe barrel.

13 Claims, 8 Drawing Sheets

SEQUENTIAL STOPPER

I. FIELD OF THE INVENTION

The invention relates to stoppers, and more particularly, to improvements in sequential stoppers which promote complete injection of a medicament held in a hypodermic syringe.

II. BACKGROUND

As is known in the art, hypodermic syringes include an elongate barrel having opposed proximal and distal ends with a chamber therebetween for receiving a fluid. A passageway extends through the distal end of the syringe barrel and communicates with the chamber. The distal end of the syringe barrel is connected to a piercing element, such as a needle cannula or a blunt cannula, for delivering fluid from the chamber and passageway. The proximal end of the syringe barrel receives a plunger rod and stopper assembly. Force applied to the plunger rod urges the stopper along the barrel to drive liquid from the chamber through the needle cannula.

Oftentimes, it is desired to deliver from the hypodermic syringe a number of discrete substances held within the chamber. These discrete substances normally must be held separate from one another until such time as delivery to the patient is desired. It is necessary, then, that the chamber defined between the proximal and distal ends of the elongate barrel be divided into a discrete number of chambers, each capable of holding a substance intended for delivery to a patient.

One way for dividing the elongate barrel into a series of discrete chambers is to employ multiple stoppers within the barrel. Each portion of the syringe barrel located between adjacent stoppers defines a discrete chamber capable of isolating a substance held in that chamber from another substance held in an adjoining chamber. One example of such syringe construction is found in U.S. Pat. No. 4,929,230 to Frederick W. Pfleger ("Pfleger '230"), whose disclosure is specifically incorporated by reference herein.

Pfleger '230 describes a particular stopper construction useful for dividing the syringe barrel into a plurality of chambers and allowing separate contents held by the syringe barrel to be sequentially administered to a patient. Making particular numerical reference to components disclosed by Pfleger '230, there is disclosed a free piston (or stopper) 33 including a hollowed chamber 48 facing the end wall 23 of the syringe barrel. Chamber 48 can be realized as a hollow circularly disposed about the central axis of stopper 33 (FIGS. 5, 6, 7) or, as shown in FIGS. 9, 10 or 11, it can assume a flattened, narrow configuration offset from the central axis of the stopper. Stopper 33 includes a closed end 34, which faces away from end wall 23 of the syringe barrel. Closed end 34 has a diameter less than the interior diameter of the syringe barrel. A peripheral side wall 35 obliquely extends between closed end 34 of stopper 33 and a cylindrical peripheral sealing surface 36 in contact with the interior surface of the syringe barrel. Oblique side wall 35 overlaps with a portion of hollowed chamber 48. It is stated at Col. 3, lines 15-17, that the oblique side wall 35 has its large end generally cylindrical, as the sealing surface 36, for sealing engagement with the syringe barrel, and it is stated at Col. 3, lines 19-23 that external ribs 37 help prevent tipping of the piston as it moves in the syringe barrel. It is believed by the inventors herein that the oblique side wall 35 is itself cylindrically formed around stopper 33 and, thus, extends about the entire circumference of the stopper. A force is generated by a proximal-most stopper 31 connected to plunger rod 30, stopper 33 will come to rest adjacent internal shoulder 25 of the syringe barrel. Continued motion by stopper 31 increases the fluid forces exerted upon oblique side wall 35 to overcome the resilient material sealing forces inherent in stopper 33. Because of the presence of hollowed chamber 48, oblique side wall 35 will collapse inwardly, allowing the fluid contents held proximally of closed end 34 to proceed in a distal direction for delivery through the needle cannula.

While generally sufficient for the purposes intended, improvements can be realized to the construction described by Pfleger '230. For example, in certain prior art hypodermic syringes, a certain amount of liquid can remain in the syringe barrel after the stoppers are advanced the full length of the barrel during an injection process. There remains in most syringes a certain residual volume, no matter how small, which is trapped between the end of the stopper and the needle tip, which includes the volume of the needle cannula and the volume presented at the distal end of the syringe barrel. A quantity of the medication can also be trapped in the area around and between the sidewalls of the stopper and the interior of the syringe barrel. In the case of expensive medications and medications requiring extreme precision and delivery, this so-called "dead space" must be overcome by overfilling the barrel in order to ensure that the proper dose is delivered. The additional medication will be disposed of with the used syringe. The costs associated with the dead volume can accumulate substantially. In the case of the design presented by Pfleger '230, it is believed that design improvements are beneficial to prevent waste of medication trapped, for example, between hollow end 48 of the stopper, internal shoulder 25 located at the extreme distal end of the syringe barrel, and outlet port 24 associated with the syringe barrel. A quantity of medication that can be held between these surfaces is seen, for instance, in FIG. 7 of Pfleger '230. Accordingly, there is a need for improvements to a sequential stopper as shown in Pfleger '230 which results in reducing the amount of medicament trapped in the syringe barrel after delivery. Such design improvements are disclosed herein.

III. SUMMARY OF THE INVENTION

A sequential stopper includes a piston-like stopper body disposed for slidable fluid-tight engagement inside the barrel of a syringe. The body has a generally cylindrical side wall with a distal end, a proximal end, and a longitudinal axis therethrough. An elongate hollow chamber is disposed within the interior of the body. Preferably, the elongate hollow chamber is disposed to one side of the longitudinal axis of the stopper body. The elongate hollow chamber includes a distal end, a proximal end, and may include an opening communicating with the distal end of the stopper body. One or more sealing elements are circumferentially disposed about the side wall of the stopper body. The circumferential sealing elements can be formed as a plurality of rings circumferentially formed about the piston-like stopper body.

The sequential stopper includes structure designed to direct substantially all of the fluid held proximally of the sequential stopper in a distal direction for substantially complete delivery to a piercing element affixed to the distal end of the syringe barrel. To this end, a pair of sealing elements are longitudinally disposed along the side wall of the stopper body in preferably parallel relation to the longitudinal axis. The pair of longitudinal sealing elements are each located along the side wall and separated by a distance at least equal to if not slightly greater than the maximum width defined by the elongate hollow chamber formed within the body.

In a preferred embodiment, the cylindrical side wall and/or the circumferential sealing elements are largely in fluid-tight contact with the interior surface of the syringe barrel. However, a portion of the cylindrical side wall is recessed from the interior surface of the syringe barrel to provide means to exert fluid pressure onto a portion of the circumferential side wall in order to cause only that portion of the circumferential side wall to collapse towards the hollow chamber, thereby establishing a fluid conduit between the distal and proximal ends of the stopper body. In a preferred embodiment, the recessed portion of the cylindrical sidewall is formed as a sloping surface adjacent the proximal end of the stopper body that is located between the pair of longitudinal sealing elements.

A distally directed, substantially conically-shaped projection is located on the distal end of the stopper body. The conically-shaped projection features a passage for directing fluid flowing through the fluid conduit established along the cylindrical sidewall towards the fluid passage of the syringe barrel. The distally-directed, conically-shaped projection can be dimensioned to substantially conform to the shape assumed by the internal shoulder located at the distal end of the syringe barrel.

In use, fluid force exerted upon the proximal-end of the stopper body causes the stopper to seat adjacent the distal end of the syringe barrel. The distally-directed, conically-shaped projection, conforming substantially to the shape of the internal shoulder located at the distal end of the syringe barrel, prevents excessive accumulation of fluid in that area. Once the stopper is seated against the distal end of the syringe barrel, increasing fluid force exerted on the recessed portion of the cylindrical sidewall causes the portion of sidewall located between the longitudinal sealing elements to collapse towards the hollow chamber. The collapse of the sidewall in this area initiates a fluid conduit between the proximal and distal ends of the stopper body restricted generally to that portion of the cylindrical sidewall located between the longitudinal sealing elements. The longitudinal sealing elements themselves, together with the portion of the circumferential sealing elements not located between the longitudinal sealing elements, remain in fluid-tight contact with the syringe barrel. Accordingly, fluid is substantially prevented from accumulating around the cylindrical side walls of the stopper body or between the distally-directed conically shaped projection and the corresponding distal end of the syringe barrel, such that fluid is substantially entirely directed through the fluid conduit for delivery through the piercing element attached to the distal end of the syringe barrel.

IV. BRIEF DESCRIPTION OF THE DRAWINGS

The invention will now be described in more detail by way of reference to the appended drawings, wherein.

V. DETAILED DESCRIPTION OF THE PREFERRED EMBODIMENT

Figure 1:
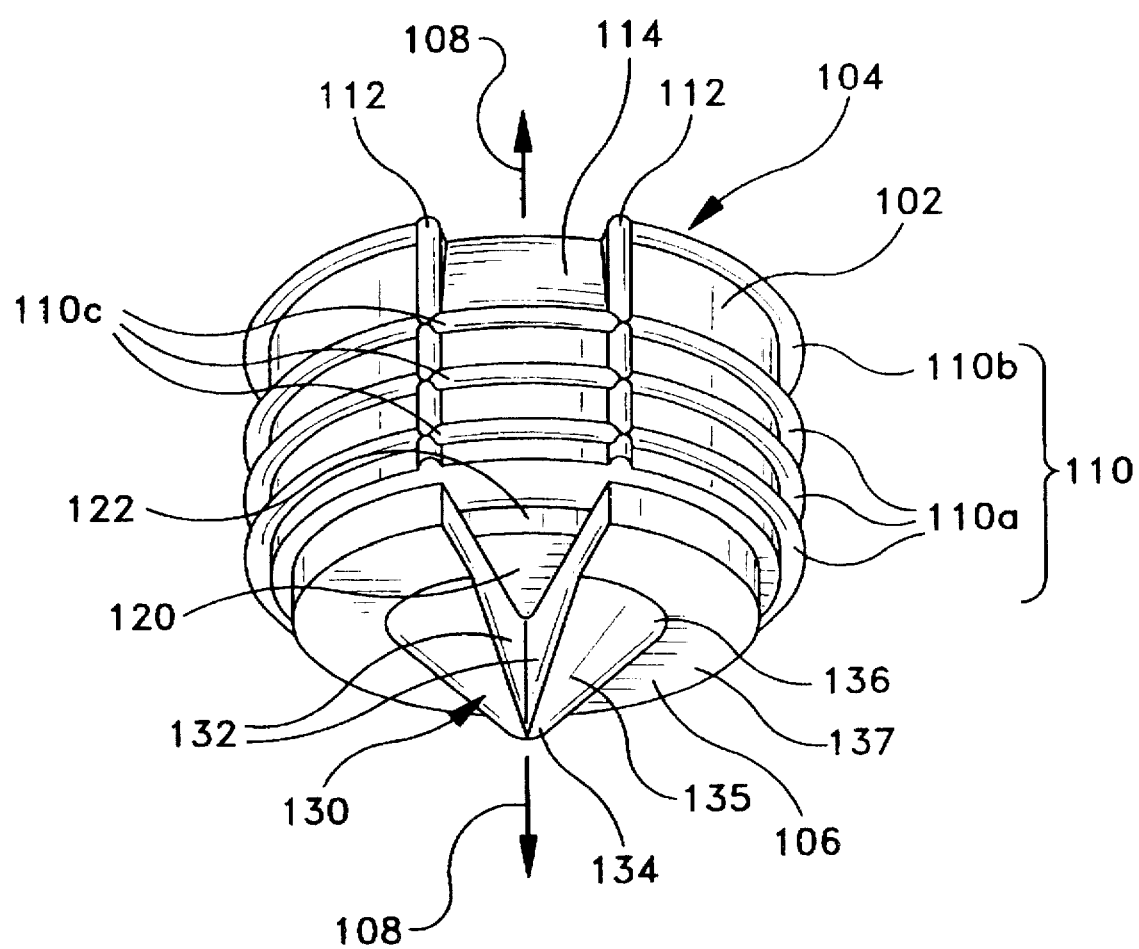
FIG. 1 is a perspective view of a sequential stopper in accordance with the present invention.

A convention used in this patent application is that the term "distal" refers to an end closer to the needle end of a syringe barrel, whereas the term "proximal" refers to an end farther away from the needle end of the syringe barrel.

Turning now to the drawings, wherein like numerals denote like components, FIGS. 1–5 depict one embodiment 100 of a sequential stopper in accordance with the present invention. Stopper 100 is formed as a piston-like stopper body displaying a generally cylindrical side wall 102 extending between a proximal end 104 and a distal end 106. Stopper 100 is characterized by longitudinal axis 108 extending through the stopper body.

Figure 5:
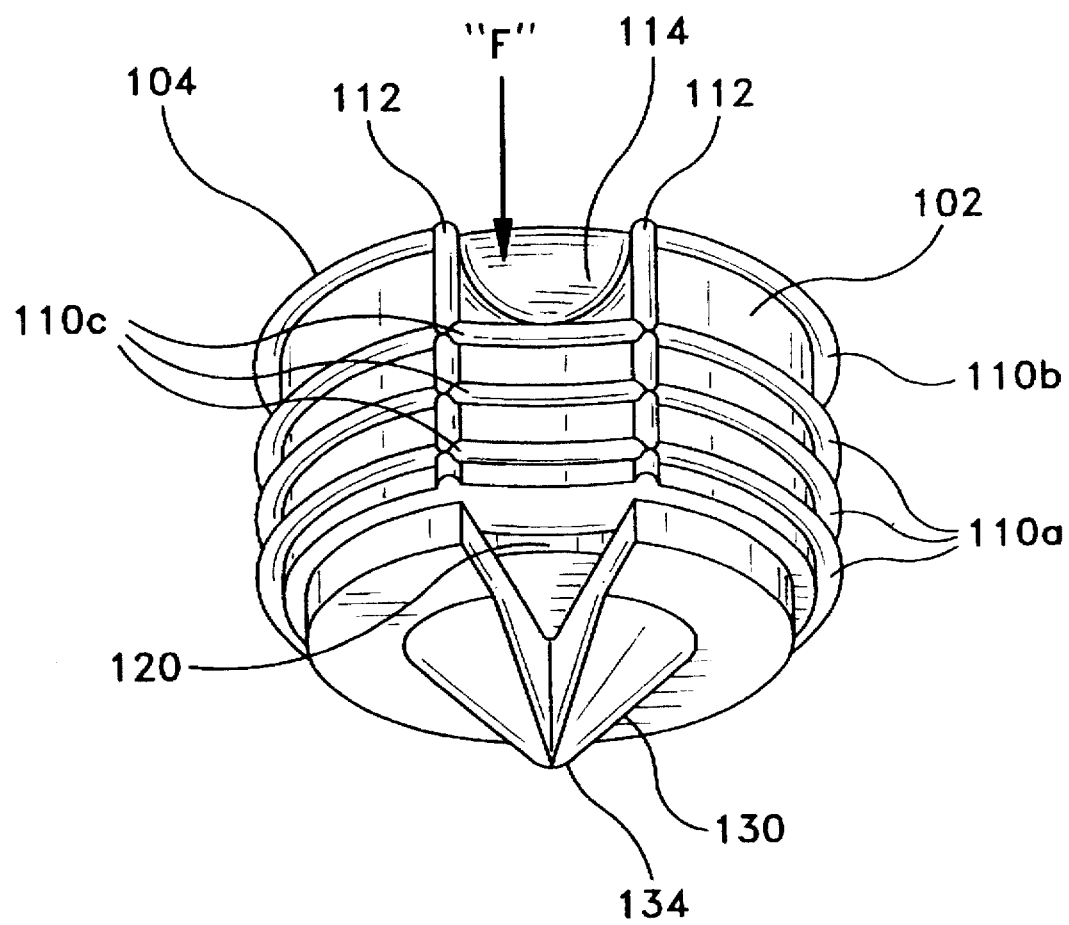
FIG. 5 is a second perspective view of the improved sequential stopper according to the invention, illustrating collapse of the side wall between the longitudinal sealing elements to establish a fluid conduit between the proximal and distal ends of the stopper.
Figure 6:
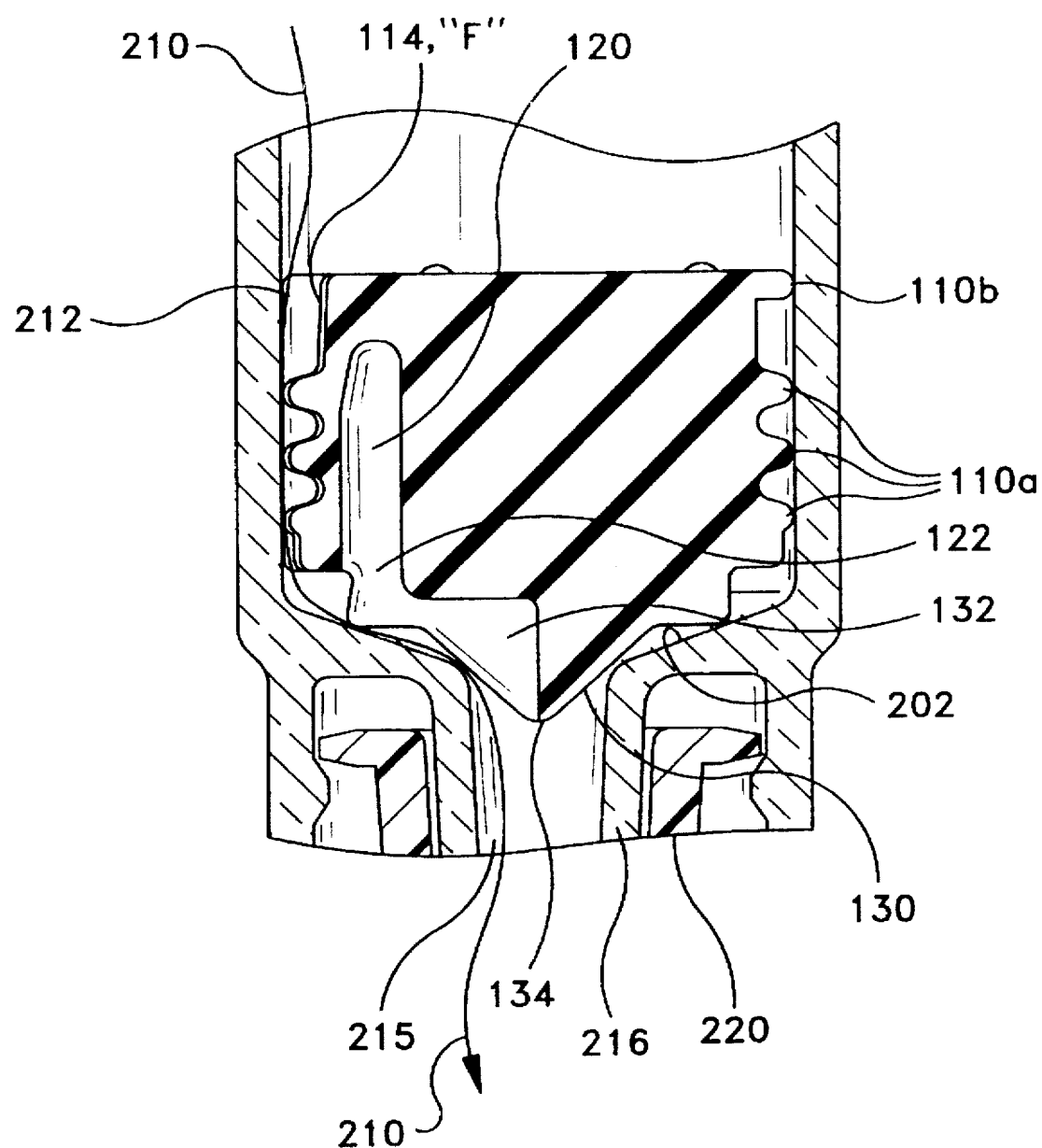
FIG. 6 is a partial cut-away view of the sequential stopper in accordance with the present invention, seated adjacent the distal end of the syringe barrel.
Figure 7:
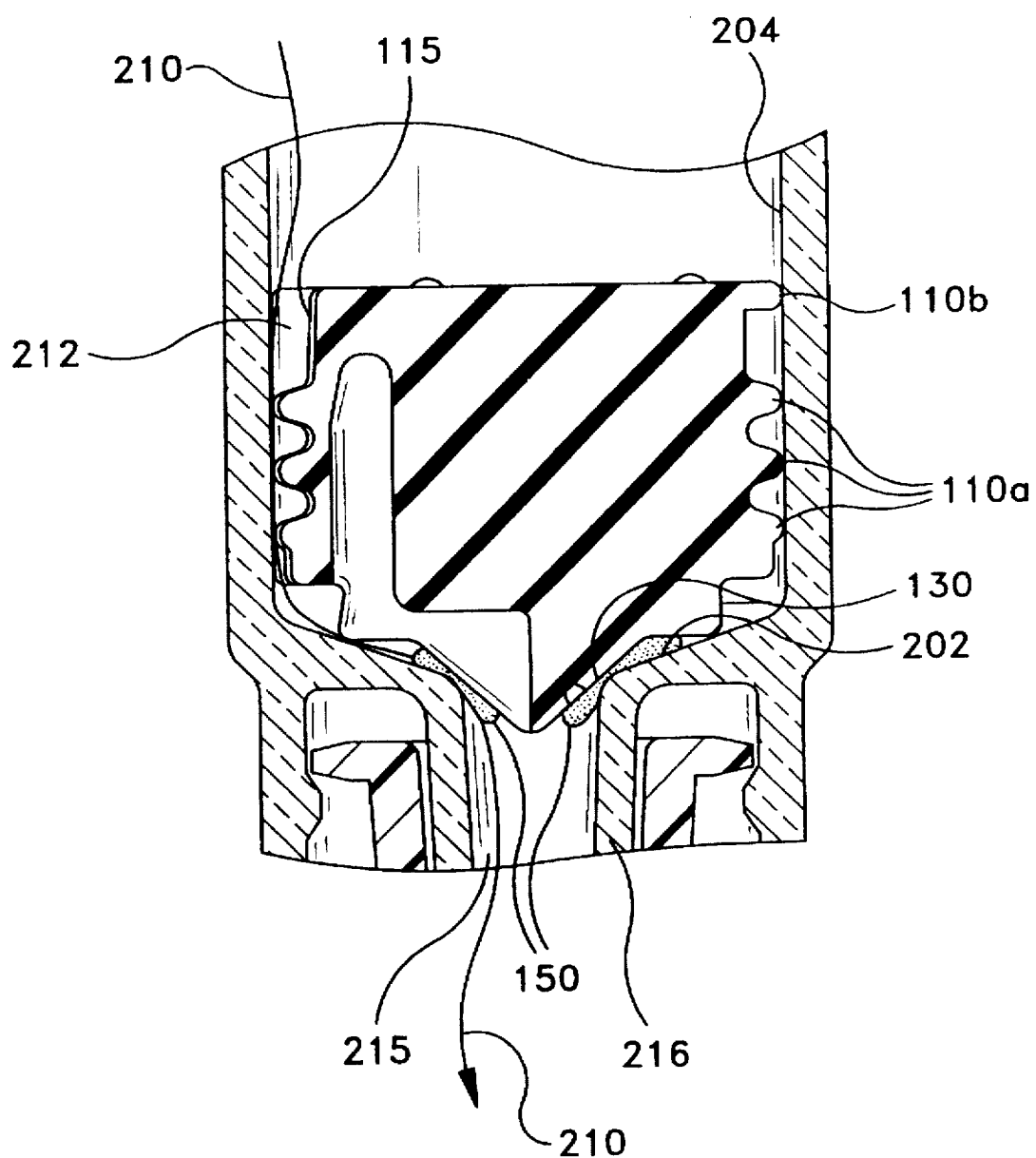
FIG. 7 is a second partial cut-away view of the sequential stopper in accordance with the present invention, incorporating a plurality of discontinuities on the distally directed conically-shaped projection.

A plurality of sealing elements may be provided on stopper 100 for sliding fluid-tight contact between the stopper and an interior surface 204 associated with a syringe barrel 200 (see, for instance, FIGS. 6 and 7). In the sequential stopper in accordance with the present invention, one or more circumferentially disposed sealing elements 110 are provided about cylindrical side wall 102. In the embodiment depicted by FIGS. 1–5, four such circumferential sealing elements 110 a,b are provided. Here, a proximal-most circumferential sealing element 110b is located adjacent proximal end 104 of the stopper such that fluid can be prevented from accumulating between cylindrical sidewall 102 and interior surface 204 in the area proximal of circumferential sealing elements 110a, themselves located intermediate the proximal and distal ends of stopper 100. It will be realized that any number of circumferential sealing elements may be chosen according to the size of the stopper and according to the needs or desires of the skilled artisan.

Figure 4:
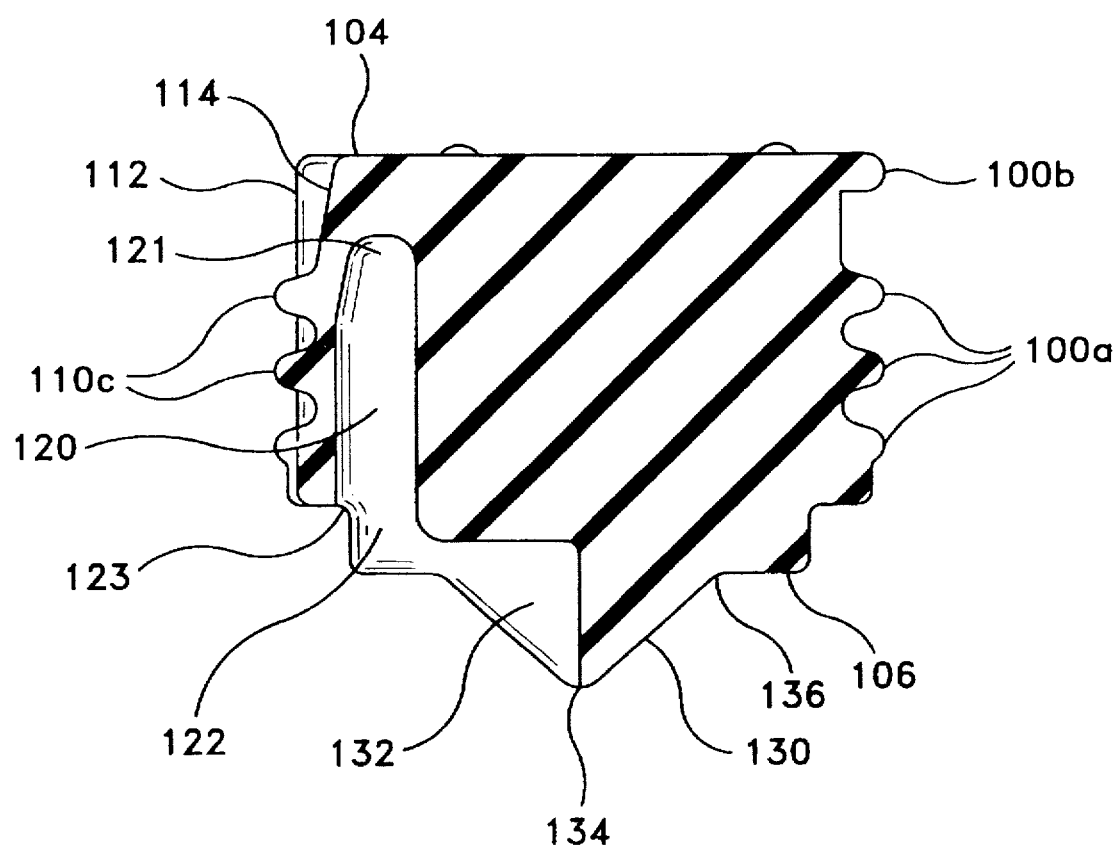
FIG. 4 is a cross-section of sequential stopper of FIG. 1, as viewed along line 4—4 of FIG. 3.

An elongate hollow chamber 120 is disposed within stopper 100 in a direction which is preferably substantially parallel to longitudinal axis 108. As best seen in FIG. 4, the elongate hollow chamber 120, which can assume a flattened shape, is preferably not concentric with longitudinal axis 108 of the stopper and is preferably disposed adjacent cylindrical side wall 102. Hollowed elongate chamber 120 features a proximal end 121 located within the interior of the stopper and a distal end 123. The purpose of elongated hollow chamber 120 is analogous to hollow chamber 48 of Pfleger '230, as previously discussed. As here shown, it is envisaged that owing to mold tooling conventionally employed to form stopper 100, distal end 123 of the chamber will communicate with distal end 106 of the stopper via an opening 122. However, it will be understood by the skilled artisan that elongate chamber 120 can be formed by other ways such that it is entirely within the stopper body without an opening 122.

Figure 2:
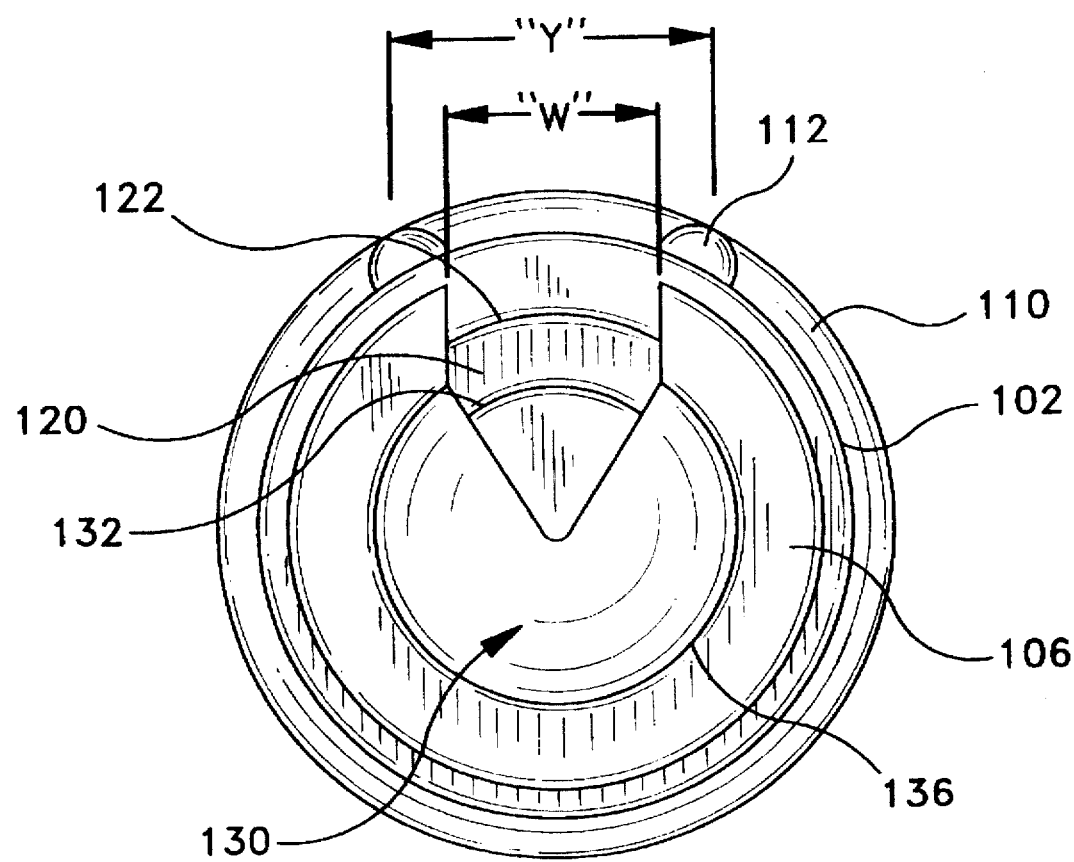
FIG. 2 is a bottom view of the sequential stopper depicted in FIG. 1.
Figure 3:
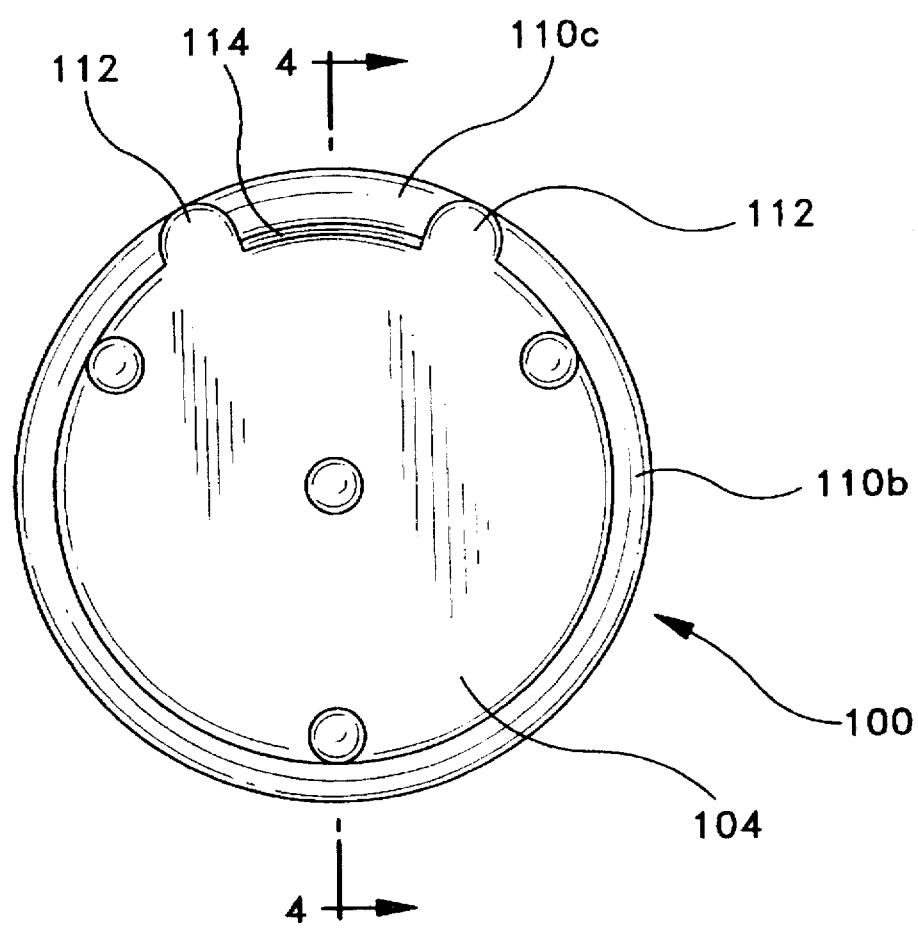
FIG. 3 is a top view of the sequential stopper depicted in FIG. 1.

Sequential stopper 100 in accordance with the present invention features structure designed to minimize a quantity of medicament trapped between stopper 100 and syringe 200 barrel that would otherwise be wasted when the syringe were disposed of following use. To this end, stopper 100 features a pair of longitudinal sealing elements 112 preferably disposed on cylindrical sidewall 102 in substantially parallel relationship with longitudinal axis 108. As best seen in FIG. 2, longitudinal sealing elements 112 are spaced from one another on cylindrical sidewall 102 by a distance "Y" that is at least equal to if not slightly greater than a maximum width "W" displayed by elongate hollow chamber 120. For the purposes of this patent application, a reference to a portion or area of cylindrical sidewall 102 that is located between longitudinal sealing elements 112 shall mean that portion or area of cylindrical sidewall 102 encompassed by distance "Y" separating the longitudinal sealing elements.

One novel aspect of the stopper in accordance with the present invention is the ability to initiate a fluid conduit 210 between the proximal and distal ends of the stopper only in the area of cylindrical sidewall 102 located between longitudinal sealing elements 112. Stopper 100 itself is disposed for sliding, fluid-tight relationship with interior surface 204 of syringe barrel 200—as here depicted, by the sliding, fluid-tight relationship between circumferential sealing elements 110a, b and interior surface 204 of the syringe barrel. One way to initiate fluid conduit 210 is to space a portion of cylindrical sidewall 102 that is adjacent proximal end 104 and between longitudinal sealing elements 112, such that this portion of the cylindrical sidewall is not in fluid-tight contact with interior surface 204. In this way, fluid force can act upon such portion of the cylindrical sidewall located between longitudinal sealing elements 112 to collapse that portion of the sidewall towards hollow chamber 120.

Figure 8:
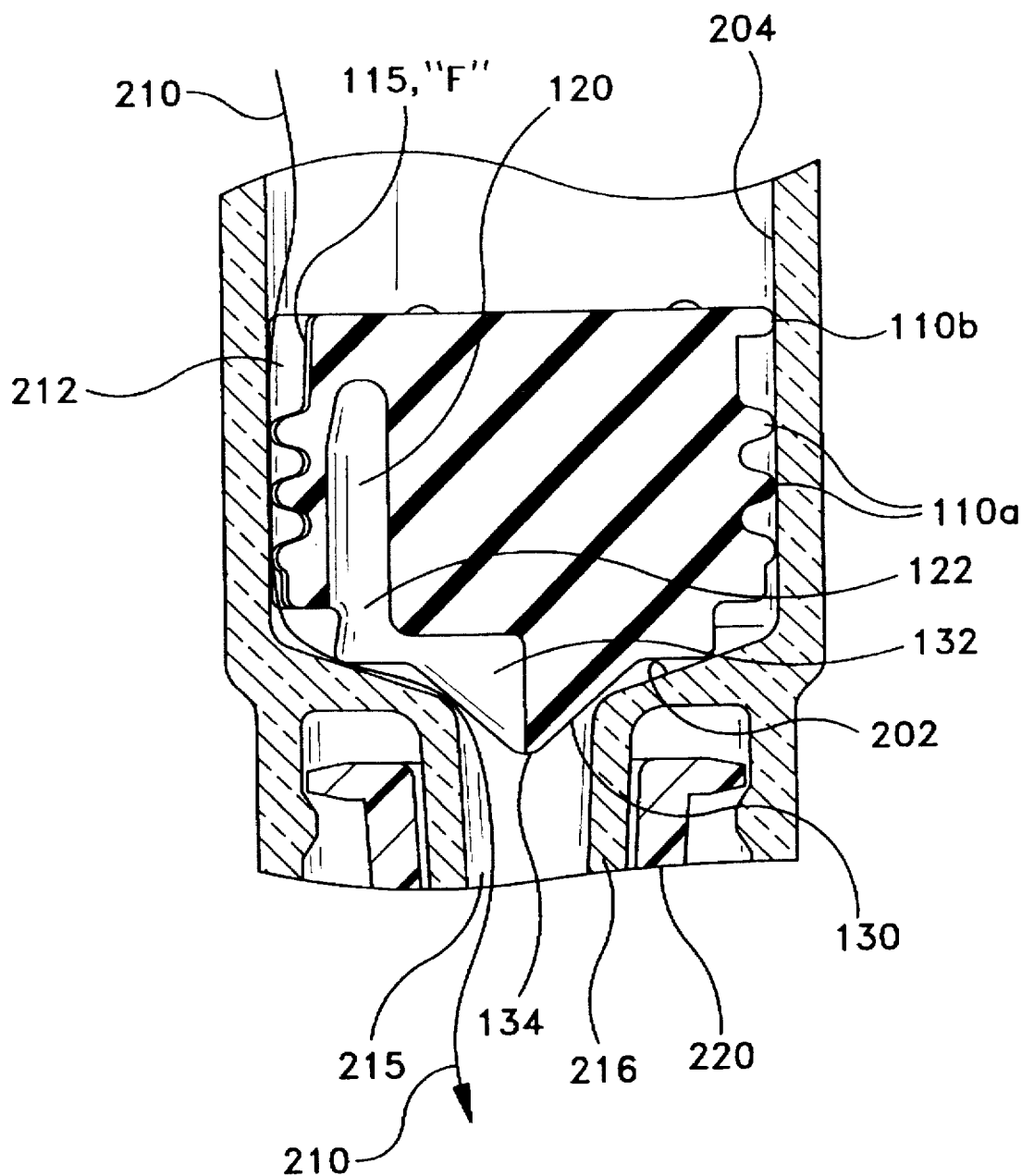
FIG. 8 depicts one way to space a portion of the cylindrical sidewall from fluid-tight contact with the interior surface of the syringe barrel.

One way to space a portion of cylindrical sidewall 102 from the interior surface of the syringe barrel is to provide a recess 115 in the sidewall, substantially aligned with longitudinal axis 108, in an area located between longitudinal sealing elements 112 and adjacent proximal end 104 (see, for instance, FIGS. 7 and 8). In the embodiment depicted in FIGS. 1–6, another way to space the sidewall from the interior surface of the syringe barrel is to provide a sloping surface 114 on cylindrical side wall 102, adjacent proximal end 104 of the stopper, in an area between the longitudinal elements. Sloping surface 114 extends obliquely outwardly on cylindrical side wall 102 from proximal end 104 to the proximal-most of circumferential sealing elements 110a. It will be noted that because of the presence of recess 115 or sloping surface 114, circumferential sealing element 110b is only partially circumferentially disposed about the stopper body such that it does not extend between longitudinal sealing elements 112.

To prevent the accumulation of fluid between distal end 106 of the stopper and distal internal shoulder 202 associated with syringe barrel 200 (see FIG. 6), stopper 100 features a distally-directed, conically-shaped projection 130. While here depicted as a conus, it will be realized that conically-shaped projection 130 can assume any shape generally approaching a conus. Conically-shaped projection 130 is characterized by a base 136 intersecting with distal end 106 of the stopper, and features a peaked tip 134 and a wall portion 135 extending between the peaked tip and the base. A channel is preferably provided in wall portion 135 to communicate fluid that passes proximally of stopper 100 with fluid passage 215 of syringe barrel 200 (see FIGS. 6–8). In one form, the channel can entail a wedge 132 extending between the proximity of peaked tip 134 and base 136 (see FIGS. 4 and 6). As seen in FIG. 4, wedge 132 is further extended to also encompass a portion of distal end face 137 of stopper 100. It will be noted that the shape and dimensions of distally-directed, conically-shaped projection 130 are preferably shaped to conform to the shape assumed by distal shoulder 202 of syringe barrel 200 in a manner to minimize any dead space between them which would otherwise trap fluid.

It will be appreciated by the skilled artisan that it may be difficult to control the shape or dimensions associated with certain portions of syringe barrel 200. One area particularly difficult to control is the bottom of the syringe barrel such as at internal shoulder 202. Accordingly, if desired, structure can be incorporated on stopper 100 between distal shoulder 202 and conically-shaped projection 130 to account for any tolerance or shape differences. Referring to FIG. 7, conically-shaped projection 130 can optionally feature one or more discontinuities, such as one or more raised-ribs 150, which act to prevent immediate sealing of fluid passage 215 in the area of internal shoulder 202. Accordingly, any liquid trapped in the space between distal shoulder 202 and conically-shaped projection 130 can run along raised ribs 150 through fluid passage 215 for delivery by needle cannula 220 attached to distal tip 216 of syringe barrel 200 (see FIG. 7). The raised ribs can be designed so as to tend to collapse at the end of the injection phase, permitting substantially full surface contact between wall portion 135 of the conical projection and distal shoulder 202 of the syringe barrel to ensure that no fluid remains trapped between them. It will also be understood by the skilled artisan that grooves may be employed in lieu of, or in combination with, ribs 150.

An advantage of stopper 100 in accordance with the present invention is that fluid is substantially prevented from being trapped between both the sidewall 102 and distal end 106 of the stopper and the interior surface 204 of the syringe barrel, in a manner that substantially all of the fluid held proximally of stopper 100 will be directed distally for delivery through fluid passage 215 associated with distal tip 216 of syringe barrel 200 (see FIG. 6). In particular, after conically-shaped projection 130 is seated adjacent internal shoulder 202 of syringe barrel 200, continued fluid force "F" exerted upon proximal end 104 will be directed to the area of sidewall 102 which is spaced from interior surface 204. For purposes of explanation but not of limitation, making reference to the structure illustrated in FIGS. 1–6, fluid force "F" will be directed to the area of sloping surface 114 (of course, it will be understood that if otherwise provided in lieu of sloping surface 114, fluid force "F" would be directed to recess 115). The absence of circumferential sealing element 110b between longitudinal sealing elements 112 allows fluid to exert force "F" upon sloping surface 114. Note that circumferential sealing elements 110 (particularly proximal-most circumferential sealing element 110b) and longitudinal sealing elements 112 remain in sealing contact with interior surface 204 of the syringe barrel to prevent fluid from being directed between interior surface 204 and cylindrical side wall 102.

Continued force "F" upon sloping surface 114 causes the sloping surface to collapse towards elongated hollow chamber 120. Collapse of sloping surface 114 towards the elongate hollowed chamber urges collapse of the portion of side wall 102 located between the longitudinal sealing elements. Particularly, sections 110c of circumferential sealing elements 110a (sections 110c are the portions of circumferential sealing elements 110a disposed between longitudinal sealing elements 112) will also separate from contact with interior surface 204 of syringe barrel 200. By ensuring that longitudinal sealing elements 112 are separated a sufficient distance "Y" with respect to maximum width "W" of chamber 120, longitudinal sealing elements 112 will themselves remain in substantial, fluid-tight contact with interior surface 204 of syringe barrel 200.

As seen then in FIGS. 5 and 6, the effect of the collapse of sloping surface 114 and separation of sections 110c from interior surface 204 of the syringe barrel is to create a fluid conduit 210 between the proximal and distal ends 104, 106 of the stopper. Fluid conduit 210 is substantially restricted to an area of the sidewall defined between longitudinal sealing elements 112. Accordingly, fluid located proximally of stopper 100 can only pass distally of stopper 100 via fluid conduit 210 for entry into fluid passage 215 of syringe barrel 200. Note that wedge 132 communicates with fluid conduit 210 to permit passage of fluid past internal shoulder 202 of the syringe barrel. By preventing the accumulation of fluid between cylindrical side wall 102 of the stopper body and interior surface 204 of syringe barrel, by substantially eliminating dead space between distal shoulder 202 of the syringe barrel and distal end 106 of the stopper, and by providing a single fluid conduit 210 between the proximal and distal ends of the stopper, substantially all of the fluid held proximally of the stopper will be directed distally through fluid passage 215 for delivery by piercing element 220.

The longitudinal and circumferential sealing elements can be formed as ribs from the same material forming stopper 100. Stopper 100 is preferably formed from suitable elastomeric materials such as rubbers or thermoplastic elastomers or other materials known to the skilled artisan that are suitable for forming syringe stoppers. The characteristics of these materials, such as elasticity, can be chosen to optimize the performance of the stopper in carrying out its various functions. The stopper and its associated components can be formed to suitable dimensions to accommodate various sizes of syringes encountered in practice. It will also be appreciated by the skilled artisan that various lubricating treatments, such as siliconizing treatments, various coating treatments such as spraying treatments, or various filming treatments such as PTFE filming treatments, can be applied to the stopper to improve sliding performance within the syringe barrel as need or desire dictate It will be appreciated and understood by those skilled in the art that further and additional forms of the invention may be devised without departing from the spirit and scope of the appended claims, the invention not being limited to the specific embodiments shown.

We claim:

1. A stopper useful for sequential delivery of contents held in the barrel of a syringe and for reducing a quantity of the contents remaining in the barrel subsequent to delivery, comprising:

a piston-like stopper body for slidable fluid-tight engagement with an inside surface of the barrel, said body having a generally cylindrical side wall with a distal end, a proximal end and a longitudinal axis therethrough;

an elongate hollow chamber disposed within said body, said hollow chamber having a distal end, a proximal end and a width;

at least one circumferential sealing element circumferentially disposed about the cylindrical side wall of the stopper body for sealing engagement with the inside surface of the syringe barrel;

a pair of longitudinal sealing elements longitudinally disposed along the side wall of the body in parallel relation to the longitudinal axis for sealing engagement with the inside surface of the syringe barrel, said pair of longitudinal sealing elements separated along the sidewall by a distance at least equal to the width of the hollow chamber;

a recessed surface provided on the cylindrical side wall of the stopper body, said recessed surface located adjacent the proximal end of the stopper body and between the pair of longitudinal sealing elements; and a distally directed, conically-shaped projection located on the distal end of the body, the conically-shaped projection having a channel communicating with a portion of the sidewall located between the pair of longitudinal sealing elements, wherein in response to fluid pressure exerted upon the proximal end of the body, said recessed surface will allow the portion of side wall located between the pair of longitudinal sealing elements to collapse towards said hollow chamber, said longitudinal sealing elements themselves remaining in fluid tight contact with the syringe barrel, to provide a fluid conduit between the proximal and distal ends of the body limited to that portion of the sidewall between the longitudinal sealing elements to direct substantially all of the fluid held proximally of the body to the distal end of the body, and wherein the channel of said conically shaped projection cooperates with said fluid conduit to expel from the syringe barrel substantially all of the fluid directed to the distal end of the body.

2. The stopper of claim 1, wherein said recessed surface comprises a sloping surface.

3. The stopper according to claim 1, wherein said at least one circumferential sealing element comprises a proximal circumferential sealing element disposed adjacent the proximal end of the stopper body.

4. The stopper according to claim 3, wherein said proximal circumferential sealing element is partially circumferentially disposed about said stopper body.

5. The stopper according to claim 1, wherein said plurality of circumferential sealing elements comprise ribs.

6. The stopper of claim 1, wherein said distally directed conically-shaped projection comprises a tip, a base located adjacent the distal end of the stopper body and a wall portion extending therebetween, wherein said channel is formed through the wall portion of the conically-shaped projection.

7. The stopper of claim 6, wherein said channel comprises a wedge extending between the base and about the proximity of the peaked tip of the conically-shaped projection.

8. The stopper of claim 7, wherein said wedge is extended to the distal end of said stopper body.

9. The stopper of claim 6, wherein said distally-directed conically-shaped projection further comprises one or more discontinuities on the wall portion.

10. The stopper of claim 9, wherein said one or more discontinuities comprises one or more ribs.

11. The stopper of claim 9, wherein said one or more discontinuities comprises one or more grooves.

12. The stopper of claim 1, wherein said stopper body is formed of an elastomeric material.

13. The stopper of claim 12, wherein said elastomeric material is selected from the group consisting of rubbers or thermoplastic elastomers.

* * * * *